United States Patent
Nycz et al.

(10) Patent No.: US 8,444,653 B2
(45) Date of Patent: May 21, 2013

(54) INTRAMEDULLARY ROD IMPLANTATION SYSTEM

(75) Inventors: Jeffrey H. Nycz, Warsaw, IN (US); Brian D. Salyer, Warsaw, IN (US); Jon C. Serbousek, Winona Lake, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 184 days.

(21) Appl. No.: 12/871,432

(22) Filed: Aug. 30, 2010

(65) Prior Publication Data

US 2012/0053585 A1    Mar. 1, 2012

(51) Int. Cl.
| | |
|---|---|
| *A61B 17/56* | (2006.01) |
| *A61B 17/58* | (2006.01) |
| *A61B 17/17* | (2006.01) |
| *A61F 2/46* | (2006.01) |
| *A61F 2/32* | (2006.01) |
| *A61F 2/36* | (2006.01) |

(52) U.S. Cl.
USPC .............. 606/98; 606/64; 606/67; 606/97; 623/22.12; 623/23.27

(58) Field of Classification Search
USPC .. 623/22.11, 22.26–23.27, 22.12; 606/62–68, 606/86 R, 96–98, 104, 102, 916
See application file for complete search history.

(56) References Cited

U.S. PATENT DOCUMENTS

| | | | |
|---|---|---|---|
| 5,049,151 A | 9/1991 | Durham et al. | |
| 5,127,913 A | 7/1992 | Thomas, Jr. | |
| 5,411,503 A | 5/1995 | Hollstien et al. | |
| 5,584,838 A | 12/1996 | Rona et al. | |
| 6,179,842 B1 * | 1/2001 | Spotorno et al. | 606/95 |
| 6,488,713 B1 * | 12/2002 | Hershberger | 623/22.11 |
| 6,499,488 B1 | 12/2002 | Hunter et al. | |
| 6,616,670 B2 | 9/2003 | Simon et al. | |
| 6,752,833 B2 * | 6/2004 | Hesseling et al. | 623/23.48 |
| 6,926,473 B2 | 8/2005 | Luebke | |
| 7,007,699 B2 | 3/2006 | Martinelli et al. | |
| 7,029,478 B2 * | 4/2006 | Hollstien et al. | 606/96 |
| 2005/0080427 A1 * | 4/2005 | Govari et al. | 606/98 |
| 2008/0086145 A1 * | 4/2008 | Sherman et al. | 606/97 |
| 2008/0195102 A1 | 8/2008 | Glazer | |
| 2009/0126997 A1 * | 5/2009 | Webb | 175/55 |

FOREIGN PATENT DOCUMENTS

WO    WO 2008105874 A1 *  9/2008

OTHER PUBLICATIONS

Andrew Parr, Industrial Control Handbook, 1998, Butterworth-Heinemann, Third Edition, p. 544.*

* cited by examiner

*Primary Examiner* — Thomas J Sweet
*Assistant Examiner* — Krutanjali M Shah
(74) *Attorney, Agent, or Firm* — Harness, Dickey

(57) ABSTRACT

A system for implanting a prosthetic device with an opening into a bone includes a plug that is removably received within the opening of the prosthetic device. The system also includes a bone removal tool that advances into the bone from outside the bone and that removes a portion of the bone while advancing into the bone to reveal the plug. The bone removal tool includes a plug engaging portion that engages with the plug. The bone removal tool at least partially removes the plug from the opening of the prosthetic device while engaged with the plug. Moreover, the system includes an alignment system that detects whether the bone removal tool and the plug are substantially axially aligned.

25 Claims, 5 Drawing Sheets

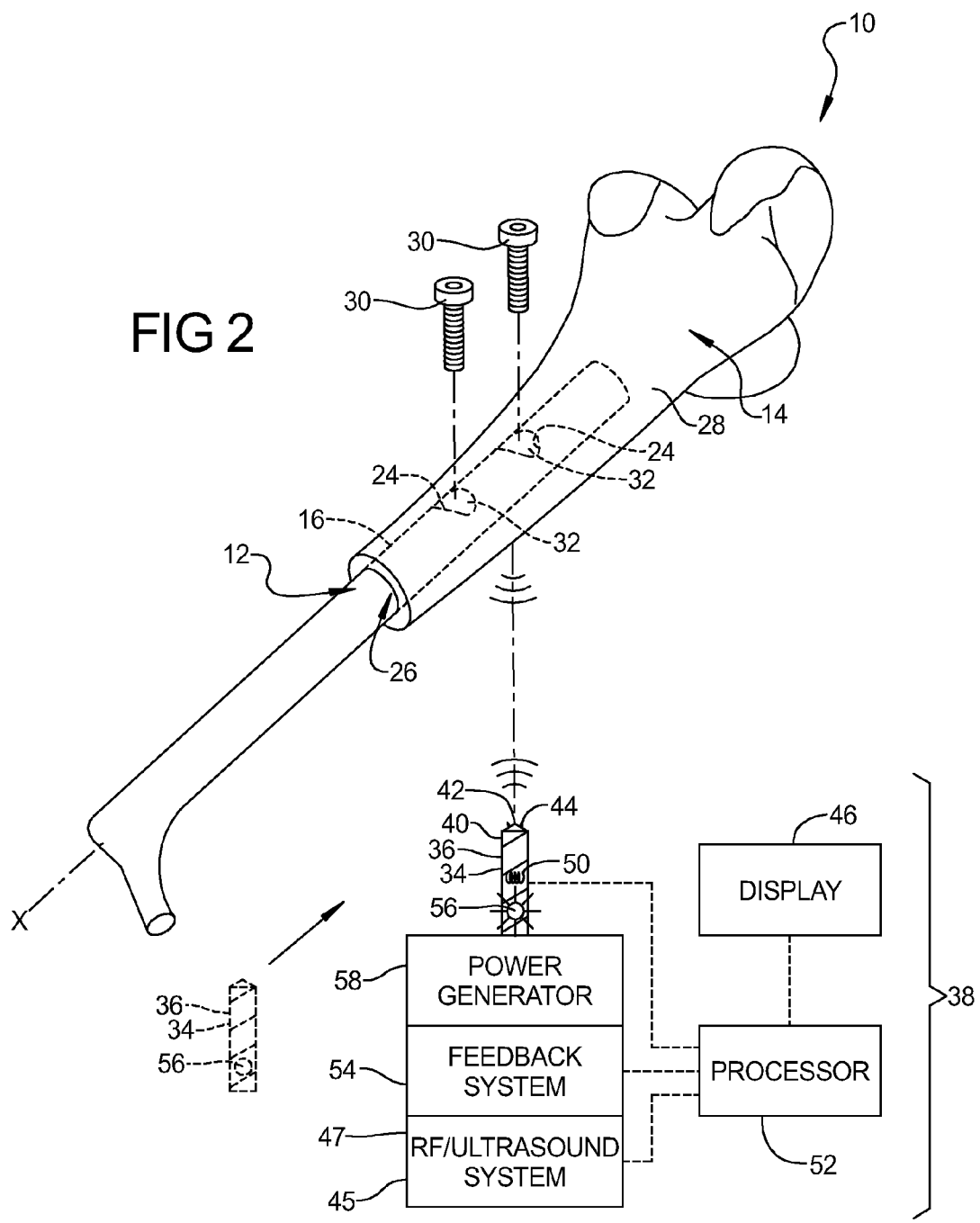

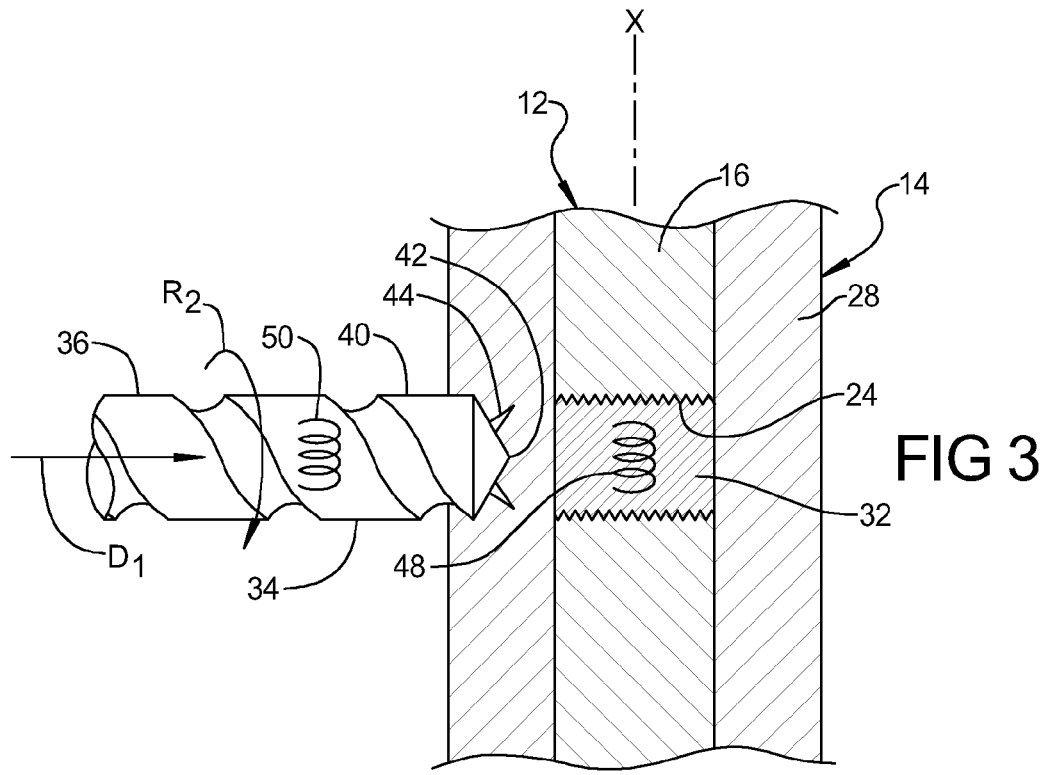
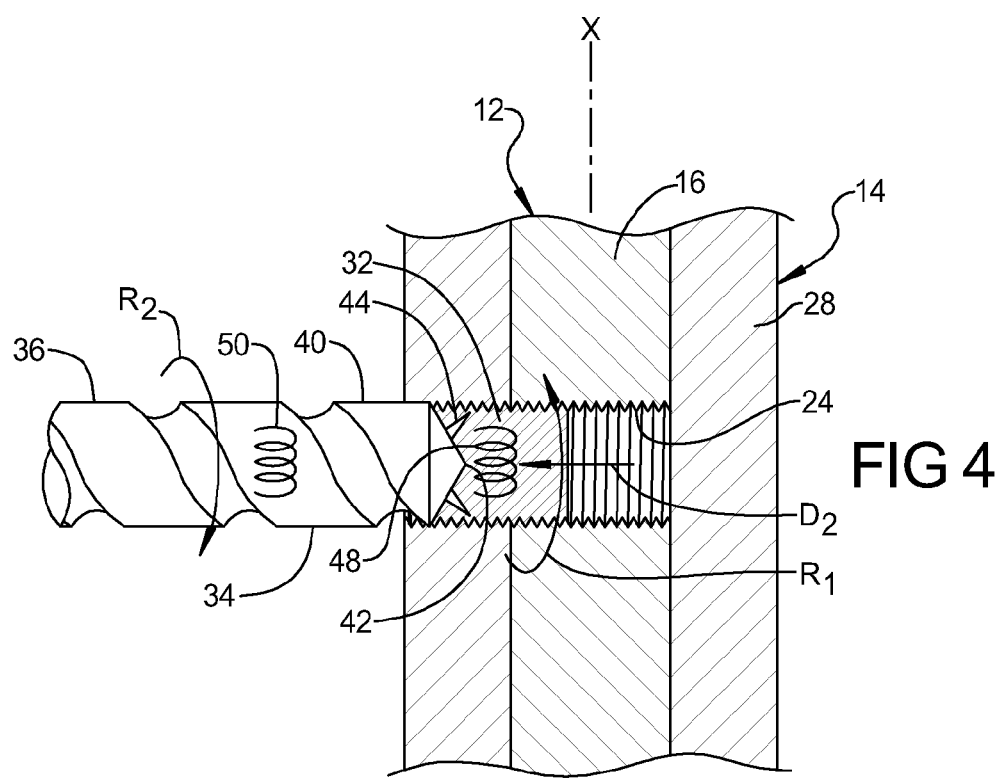

INTRAMEDULLARY ROD IMPLANTATION SYSTEM

FIELD

The following relates to an intramedullary rod and, more specifically, relates to an intramedullary rod implantation system.

BACKGROUND

The statements in this section merely provide background information related to the present disclosure and may not constitute prior art.

Prosthetic devices can be implanted in a patient's body in a variety of ways. For instance, some prosthetic devices include portions that are implanted in the intramedullary (IM) canal of a bone. In one specific example, a femoral component of a hip joint prosthesis can include an IM rod that is implanted coaxially within the IM canal of a resected femur. Also, fasteners can extend through the cortical and cancellous material of the femur, transverse to the axes of the rod and femur, and the fasteners can extend into respective holes that are formed in the rod. Accordingly, the IM rod can be frictionally fit within the IM canal, and the fasteners can further secure the IM rod to the femur.

During the implantation procedure, after the IM rod is implanted in the IM canal, holes can be drilled transversely through the cortical and cancellous material of the femur to reveal the holes in the IM rod and to provide access for the transverse fasteners. However, determining where to drill can be difficult. Accordingly, the following disclosure relates to a system for more easily determining where to drill to provide access to the transverse holes.

SUMMARY

A system for implanting a prosthetic device into a bone is disclosed. The prosthetic device has an opening that is disposed in the bone. The system includes a plug that is removably received within the opening of the prosthetic device. The system also includes a bone removal tool that advances into the bone from outside the bone and that removes a portion of the bone while advancing into the bone to reveal the plug. The bone removal tool includes a plug engaging portion that engages with the plug. The bone removal tool at least partially removes the plug from the opening of the prosthetic device while engaged with the plug. Moreover, the system includes an alignment system that detects whether the bone removal tool and the plug are substantially axially aligned.

In addition, a method of implanting a prosthetic device into a bone is disclosed. The method includes inserting the prosthetic device into the bone. The prosthetic device includes an opening and a plug removably received within the opening. The method also includes detecting whether a bone removal tool outside the bone and the plug are substantially axially aligned. Moreover, the method includes advancing the bone removal tool from outside the bone into the bone to remove a portion of the bone and to reveal the plug. Additionally, the method includes engaging the bone removal tool and the plug, and removing the plug from the opening of the prosthetic device at least partially while the bone removal tool is engaged with the plug.

Still further, a system for implanting a prosthetic device into a bone is disclosed. The system includes an intramedullary (IM) rod that is operable to be implanted in an IM canal of a femur, a tibia, or a humerus. The IM rod has a longitudinal axis and a through hole that extends transverse to the longitudinal axis. The system also includes a plug that is threadably engaged to the IM rod within the through hole in a first rotational direction. The system also includes a bone removal tool that rotates in a second rotational direction. The second rotational direction is opposite from the first rotational direction. The bone removal tool advances through the bone from outside the bone in a first linear direction and removes a portion of the bone while rotating in the second rotational direction and while advancing into the bone in a first linear direction to reveal the plug. The bone removal tool includes a barb that embeds within and engages with the plug. The bone removal tool at least partially threadably disengages the plug from the through hole of the IM rod while rotating in the second rotational direction and while embedded within the plug. Moreover, the system includes an alignment system that detects whether the bone removal tool and the plug are substantially axially aligned. The alignment system includes an ultrasound system and/or a proximity sensor, and the alignment system includes a power generating device that generates power from rotation of the bone removal tool to power the alignment system. In addition, the system includes a feedback device that indicates that the bone removal tool and the plug are substantially axially aligned. Also, the system includes a fastener that extends into the bone and into the opening to secure the IM rod to the bone.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 2 is an assembled, perspective view of the system of FIG. 1;

FIG. 3 is a sectional view of the system of FIG. 1, wherein a bone removal tool is shown removing a portion of bone in order to reveal a plug within an intramedullary rod;

FIG. 4 is a sectional view of the system of FIG. 1, wherein the bone removal tool of FIG. 3 is shown engaged with the plug and removing the plug from the IM rod;

DETAILED DESCRIPTION

Figure 1:
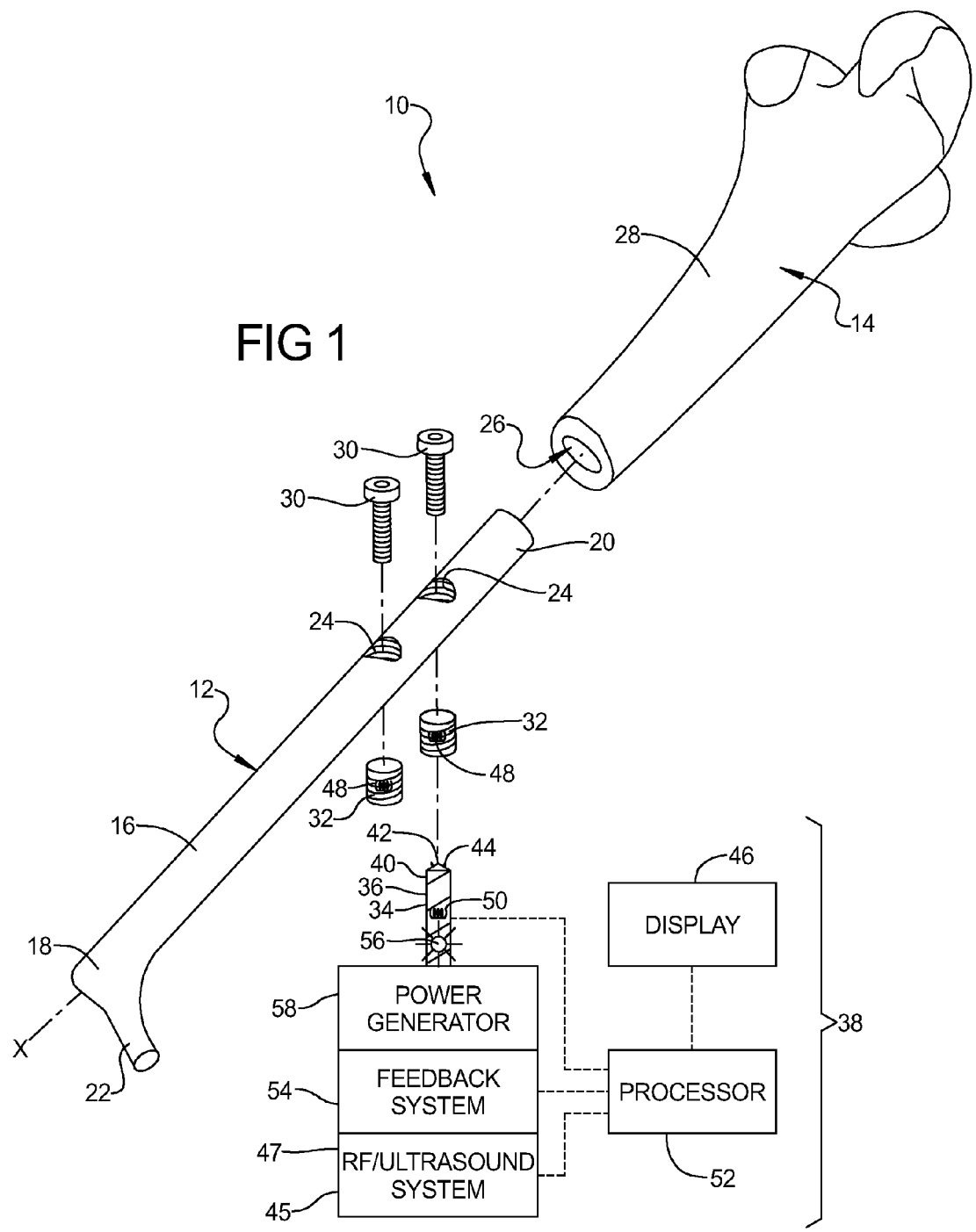
FIG. 1 is an exploded, perspective view of a system for implanting a prosthetic device according to various embodiments of the present disclosure.

The following description is merely exemplary in nature and is not intended to limit the present disclosure, application, or uses. Moreover, while the exemplary embodiments herein are directed to an intramedullary rod, the present disclosure can be directed to any implant having openings that need to be located for implantation. It should be further understood that throughout the drawings, corresponding reference numerals indicate like or corresponding parts and features.

Referring initially to FIG. 1, a system 10 for implanting a prosthetic device 12 into a bone 14 is illustrated, according to various exemplary embodiments of the present disclosure. In the embodiments illustrated, the prosthetic device 12 can be an elongated implant, such as an intramedullary (IM) rod 16 for a femoral implant of a prosthetic joint assembly. However, it will be appreciated that the device 12 can be a stem, a segmented replacement, a modular implant, or any other prosthetic device 12 that is implanted in a femur or any other bone.

The IM rod 16 can be elongate and can have a substantially straight or curved longitudinal axis X. The rod 16 can include a proximal end 18 and a distal end 20. Furthermore, the IM rod 16 can include a neck 22, which is disposed on the proximal end 18. The neck 22 can receive a head (not shown), which is received for rotation within an acetabular cup (not shown) of the patient. Other configurations of an IM rod 16 can also be employed without departing from the scope of the present disclosure.

As shown in FIG. 1, the IM rod 16 can also include at least one transverse opening 24. In some embodiments, the IM rod 16 can include two or more openings 24, and the openings 24 can be disposed between the proximal and distal ends 18, 20. Furthermore, the openings 24 can be through holes that extend transverse (e.g., perpendicular) to the axis X of the rod 16. In other embodiments, the openings 24 can extend through the rod 16 at any suitable acute angle relative to the axis X of the rod 16. The openings 24 can be internally threaded. It will be appreciated that the openings 24 can be of any suitable type other than through holes (e.g., elongated slots, etc.). Also, it will be appreciated that there can be any number of openings 24 in the rod 16.

As shown in FIG. 2, the rod 16 can be inserted into an IM canal 26 within a resected femur 28. In order to further secure the rod 16 to the femur 28, fasteners 30 can each extend transversely through cortical and cancellous bone of the femur 28 and into a respective opening 24. In some embodiments, the fasteners 30 can be threaded fasteners (e.g., screws, etc.) and can threadably engage to the rod 16 within the threaded openings 24. The fasteners 30 can be of any suitable type other than threaded fasteners 30 (e.g., transverse pins, etc.).

It will again be appreciated that the system 10 can be used for implanting any type of prosthetic device 12 other than a femoral implant. Also, it will be appreciated that the system 10 can be used for implanting a prosthetic device 12 into any bone 14 other than a femur 28. For instances, the system 10 can be used for implanting a prosthetic device 12 into a tibia or humerus without departing from the present disclosure. Moreover, it will be appreciated that the system 10 can be used for implanting any prosthetic device 12 into any location in a bone 14 other than an IM canal 26.

In order to implant the prosthetic device 12, the femur 28 can be resected, and the rod 16 can be driven longitudinally into the canal 26. Then, a bone removal tool 34, such as a drill bit 36, mill, or other suitable tool, can be used to remove bone and form holes to reveal and provide access for the fasteners 30 to extend into the openings 24. More specifically, the drill bit 36 can rotate about its axis to advance through the bone 14 from outside the bone 14 and to remove a portion of the bone 14 to reveal one of the openings 24.

To assist the user in locating the openings 24 before drilling, the system 10 can include plugs 32, which are removably and threadably received within the openings 24. In some embodiments, the system 10 can include a plug 32 for each opening 24. The plugs 32 can be attached to the rod 16 within the respective openings 24 before the rod 16 is inserted within the canal 26 and before drilling.

Moreover, the system 10 can include an alignment system 38 that detects whether the bone removal tool 34 and any of the plugs 32 are substantially axially aligned, as will be discussed in greater detail below. Accordingly, the system 10 can assist the surgeon when attempting to align the bone removal tool 34 and the plugs 32, and the system 10 can allow the surgeon to implant the rod 16 in the bone 14 more quickly, conveniently, and accurately as will be discussed.

Referring now to FIGS. 1-4, the plugs 32 will be discussed in greater detail. As shown, the plugs 32 can be substantially cylindrical and can be either solid or hollow. The plugs 32 can be made out of any suitable material. For instance, the plugs 32 can include an ultrasonically sensitive material (e.g., magnesium, cobalt chrome, alloys thereof, etc.) or any other suitable material. In some embodiments, the plugs 32 can be made of a material that is different from the rod 16 such that the plugs 32 can be distinguished from the rod 16 using ultrasound as will be discussed in greater detail below. Also, the plugs 32 can be made out of a pierceable, malleable, or deformable material (e.g., Delrin, nylon, etc.) such that the drill bit 36 can embed within the plugs 32 as will be discussed in greater detail below. Furthermore, the plugs 32 can be threaded so as to threadably engage to the rod 16 within the openings 24. In some embodiments, the plugs 32 can include self-tapping threads. It will be appreciated, however, that the plugs 32 can be removably coupled to the rod 16 in any other suitable fashion. Also, the plugs 32 can be attached to the rod 16 and shipped as such by the manufacturer or the plugs 32 can be attached to the rod 16 by the surgeon or other medical professional (e.g., intra-operatively).

In addition, the drill bit 36 can include sharpened flutes 40 that extend helically about the axis at the drill bit 36. Also, the drill bit 36 can be a commercially available drill bit 36 that has been modified to include features discussed below. During operation, the drill bit 36 can rotate about its longitudinal axis, and can drill through and remove portions of the bone 14 to form holes therein.

As best shown in FIGS. 3 and 4, the drill bit 36 can include a plug engaging portion, such as one or more barbs 44 that extend from a terminal distal end 42 of the drill bit 36. The barbs 44 can allow the drill bit 36 to engage with the plug 32 (FIG. 4) and embed into the plug 32. As will be discussed, when the drill bit 36 is engaged with the plug 32, the drill bit 36 can be used to at least partially remove the plug 32 from the opening 24. It will be appreciated that the drill bit 36 can include any suitable plug engaging portion other than the barbs 44 without departing from the scope of the present disclosure. For instance, the drill bit 36 can include a helical projection that pierces and embeds within the plug 32, the drill bit 36 can includes conventional flutes that embed within the plug 32, or the drill bit 36 can include any other suitable feature for embedding within the plug 32.

As shown in FIG. 4, the plugs 32 can be threadably engaged to the rod 16 in the opening 24 in a first rotational direction R1, and the drill bit 36 can drill in the bone 14 by rotating in a second rotational direction R2, and the first and second rotational directions R1, R2 can be opposite to each other. More specifically, in some embodiments, the threading on the plug 32 and in the opening 24 can be left-handed threading, and the flutes 40 on the drill bit 36 can be right-handed fluting.

Thus, as shown in FIG. 3, the drill bit 36 can be advanced in a first linear direction D1 and rotated in the second (right-handed) rotational direction R2 to tunnel into the bone 14 and to advance toward the plug 32. As shown in FIG. 4, upon reaching the plug 32, the drill bit 36 can embed within the plug 32 by way of the barbs 44. Because of the left-handed threading in the first rotational direction R1 of the plug 32 and opening 24, the right-handed rotation of the drill bit in the second rotational direction R2 can cause the plug 32 to be backed out of the opening 24 and to move at least partially in the second linear direction D2, away from the rod 16. Therefore, the drill bit 36, itself, can be used to remove the plug 32. (In other words, the drill bit 36 can drill into the bone 14 toward the plug 32 in the first linear direction D1 (FIG. 3), and the drill bit 36 and the plug 32 can be backed out of the bone 14 in the second, opposite linear direction D2 (FIG. 4) by continuing the rotation of the drill bit 36 in the second rotational direction R2).

It will be appreciated that the fluting on the drill bit 36 can be left-handed without departing from the scope of the present disclosure. Likewise, it will be appreciated that the threading on the plug 32 and opening 24 can be right-handed without departing from the scope of the present disclosure.

Referring now to FIGS. 1 and 2, the alignment system 38 will be discussed in greater detail. In some embodiments, the alignment system 38 can include an ultrasound system 45. The ultrasound system 45 can be operably coupled to the bone removal tool 34. The ultrasound system 45 can also include a display 46 and a processor 52. As shown in FIG. 2, the ultrasound system 45 can generate and emit an ultrasound signal directed away from the drill bit 36 and in an axial direction of the drill bit 36. Accordingly, the ultrasonic signal generated by the system 45 can reflect from the bone 14, the rod 16, and the plug 32, and the reflected signal can be received by the ultrasound system 45 and processed by the processor 52 to create an image that is displayed on the display 46.

As mentioned above, the plug 32 can be made of and/or include an ultrasonically detectable material, such as magnesium, cobalt chrome, or any other alloy thereof. Also as mentioned, the plug 32 can be made of a material that is different from the material of the rod 16. Thus, the plug 32 can have a different ultrasonic signature from adjacent areas of the rod 16, the bone 14, etc. due to the presence of the ultrasonically detectable material in the plug 32. For instance, the plug 32 can have a different contrast on the display 46 from adjacent areas of the rod 16 and bone 14. With the image on the display 46, the user can determine whether the drill bit 36 and the plug 32 are substantially axially aligned in real time. Once aligned, the drill bit 36 can be used to drill into the bone 14 and remove the plugs 32, as discussed above.

In addition to or as an alternative to the ultrasound system 45, the alignment system 38 can include a proximity sensor system 47 (e.g., RFID system). For instance, in some embodiments, the proximity sensor system 47 can include a signal generator 48 that is operatively coupled to the plug 32 or the drill bit 36. As shown in FIGS. 3 and 4, the signal generator 48 can be enclosed within or otherwise operably coupled to the plug 32. Moreover, the alignment system 38 can include a receiver 50. The signal generator 48 can generate and emit a radio frequency (RF) signal at any suitable frequency, and the receiver 50 can receive the radio signal that is emitted when the receiver 50 is in relatively close proximity (e.g., aligned with and disposed just outside the bone 14). Moreover, the processor 52 can process the signal received by the receiver 50 to thereby automatically detect that the drill bit 36 is substantially aligned with the plug 32.

The signal generator 48 can be a passive element (e.g., includes no power source), and the receiver 50 can be a transceiver that emits an electromagnetic field that causes the signal generator 48 to generate a current, thereby causing the signal generator 48 to emit the RF signal described above. In other embodiments, the signal generator 48 can be an active element (e.g., includes a power source) that independently generates and transmits the RF signal described above.

Thus, assuming that the signal generator 48 is a passive element, the user can move the drill bit 36 relative to the plug 32, and when the drill bit 36 is misaligned and spaced from the plug 32 (shown in phantom in FIG. 2), the signal generator 48 will not emit the RF signal; however, when the drill bit 36 is substantially axially aligned with the plug 32 just outside the bone 14 (shown in solid lines in FIG. 2), the signal generator 48 will emit the RF signal, and the receiver 50 will receive the signal emitted by the generator 48. As a result, the processor 52 processes the signal received by the receiver 50 to detect that the drill bit 36 is in axial alignment with the plug 32.

It will be appreciated that the alignment system 38 can include any suitable means for detecting alignment of the drill bit 36 and the plug 32 without departing from the scope of the present disclosure. For instance, the alignment system 38 can include any suitable means in addition to or instead of the ultrasonic system and the proximity sensor system described above.

As shown in FIGS. 1 and 2, the system 10 can also include a feedback device 54. The feedback device 54 can include an indicator 56. The indicator 56 of the feedback device 54 can selectively provide a feedback signal to indicate that the drill bit 36 is substantially aligned with the plug 32. The indicator 56 can provide a visual feedback signal (e.g., a light, etc.), an audible signal (e.g., a sound, etc.), and/or a tactile feedback signal (e.g., vibration, etc.). However, it will be appreciated that the feedback device 54 can provide any suitable feedback signal and/or any combination of feedback signals. In some embodiments, the indicator 56 can be mounted directly to the drill bit 36. For instance, the indicator 56 can be an LED light that is embedded in a groove on or otherwise attached to the drill bit 36. Thus, as the drill bit 36 rotates, the indicator 56 can appear to be a continuous ring of light such that the indicator 56 is fairly easy to see for the user. However, the indicator 56 could be incorporated within the display 46 or in any other suitable location without departing from the present disclosure. The feedback signal provided by the indicator 56 can be triggered by the alignment system 38.

Thus, as shown in FIG. 2, when the alignment system 38 detects that the drill bit 36 is misaligned and spaced away from the plug 32 (as shown in phantom), the indicator 56 will not provide the feedback signal. However, when the alignment system 38 detects that the drill bit 36 is substantially aligned with the plug 32, the indicator 56 can provide the feedback signal. In some embodiments, the indicator 56 can provide multiple feedback signals. For instance, the indicator 56 can provide a first feedback signal (e.g., a red light) when the drill bit 36 is spaced far away from the plug 32, the indicator 56 can provide a second feedback signal (e.g., a yellow light) when the drill bit 36 is close, but axially misaligned from the plug 32, and the indicator 56 can provide a third feedback signal (e.g., a green light) when the drill bit 36 is axially aligned with the plug 32. Thus, the feedback device 54 can conveniently indicate to the user that the drill bit 36 is in alignment.

Furthermore, the system 10 can include a power generator 58. The power generator 58 can be of any suitable type, such as a piezoelectric device. The power generator 58 can generate power due to rotation of the drill bit 36, and the generated power can be used to power the ultrasound system 45, the feedback device 54, the indicator 56, the alignment system 38, or any other suitable component of the system 10. In some embodiments, a commercially available drill bit 36 can be retrofitted with the power generator 58.

Thus, during use, the plug 32 can be secured to the rod 16, and the rod 16 can be implanted into the resected bone 14. Then, the drill bit 36 can be moved relative to the bone 14 until the indicator 56 indicates that the drill bit 36 is in alignment with the openings 24 and the plugs 32 therein. Then, the user can drill through the bone 14 and embed the drill bit 36 into the plug 32. Further rotation of the drill bit 36 can cause the plug 32 to back out of the opening 24, as described above, and the plug 32 can be fully removed from the rod 16 and the bone 14. In some embodiments, the drill bit 36 only partially removes the plugs 32 and a separate tool is used to fully remove the plugs 32 from the rod 16 and bone 14. Once the plugs 32 are removed, the drill bit 36 or another drill bit can be advanced into both the bone 14 and the openings 24 to provide full clearance for the fasteners 30. It will be appreciated that the holes created by the drill bit 36 for removing the plugs 32 can be used as a pilot hole for creating holes for the fasteners 30.

Accordingly, the system 10 can allow the user to quickly and accurately locate the openings 24 in the rod 16. Moreover, the drill bit 36 can be used to remove the plugs 32. As such, fewer tools are needed to locate the openings 24 and provide access to the openings 24.

Figure 5:
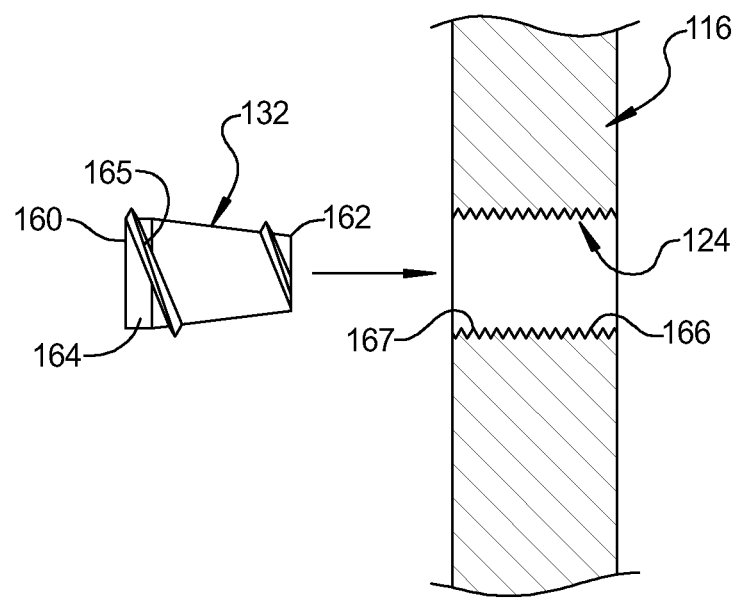
FIG. 5 is a partial sectional view of the system according to various additional exemplary embodiments, wherein a plug is shown before being coupled to an intramedullary (IM) rod.
Figure 6:
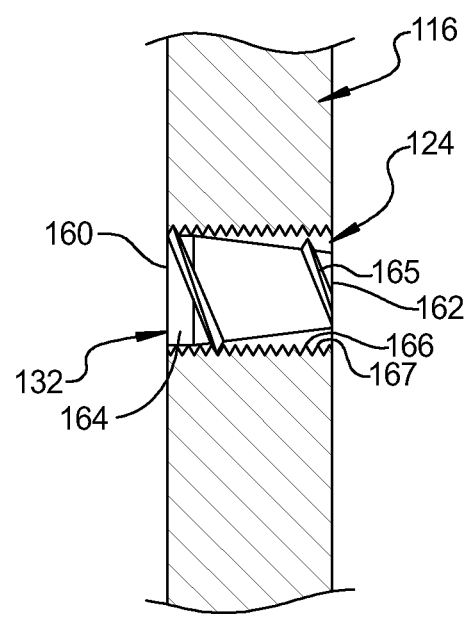
FIG. 6 is a partial sectional view of the system of FIG. 5, wherein the plug is shown coupled to the IM rod.

Referring now to FIGS. 5 and 6, additional exemplary embodiments of the present disclosure will be discussed. Components that are similar to the embodiments of FIGS. 1-4 are identified with corresponding reference numerals increased by 100. It will be appreciated that the components illustrated in FIGS. 5 and 6 can include similar features, can be made out of similar materials, and can provide similar advantages as those described above. Those details will not be repeated here; however, the embodiments of FIGS. 5 and 6 can include additional features as well, including those discussed below.

FIG. 5 shows an exemplary embodiment of the plug 132 before being inserted into the opening 124 of the rod 116. As shown, the plug 132 can be axially tapered. For example, the plug 132 can include a first end 160 and a second end 162, and the plug 132 can gradually taper down in width from the first end 160 to the second end 162. Also, the plug 132 can include a thread 165. As shown, the pitch of the thread 165 can be significantly higher than threading 167 on the inner surface 166 of the opening 124 in the rod 116.

Thus, when the second end 162 of the plug 132 is inserted and advanced into the opening 124 (indicated by an arrow in FIG. 5), the thread 165 can guide movement of the plug 132 into the opening 124, and the tapered outer surface 164 of the plug 132 can abut against the inner surface 166 of the opening 124 to center the plug 132 within the opening 124. Accordingly, inserting the plug 132 into the rod 116 can be facilitated.

As shown in FIGS. 5 and 6, the outer surface 164 of the plug 132 can be at least partially deformable. For instance, the plug 132 can be made of a biocompatible material that is softer than that of the rod 116, and the outer surface 164 adjacent the first end 160 can plastically deform against the inner surface 166 of the opening 124 upon insertion of the plug 132 into the opening 124. For instance, the outer surface 164 can plastically deform into the threading of the inner surface 166 of the opening 124 to securely engage the rod 116. In other embodiments, the plug 132 can elastically deform against the inner surface 166 of the opening 124 upon insertion of the plug 132.

Furthermore, because of the tapered outer surface 164, only a portion of the plug 132 (i.e., the portion adjacent the first end 160, separated by a vertical line in FIG. 6) engages the inner surface 166 of the tapered plug 132. As a result, the plug 132 can be easier to disengage and remove from the rod 116. Also, the plug 132 is unlikely to disengage from or be stripped by the removal tool 34 (FIGS. 3 and 4) because the plug 132 can disengage from the rod 116 with less resistance.

In addition, in some embodiments, the thread 165 of the plug 132 and/or the threading 167 of the opening 124 can have a significantly high thread pitch.

For instance, the thread pitch can be high enough such that backing out the plug 132 of the opening 124 and disengaging the plug 132 from the rod 116 can be accomplished simply by rotating the plug 132 less than one full rotation about its axis.

Figure 7:
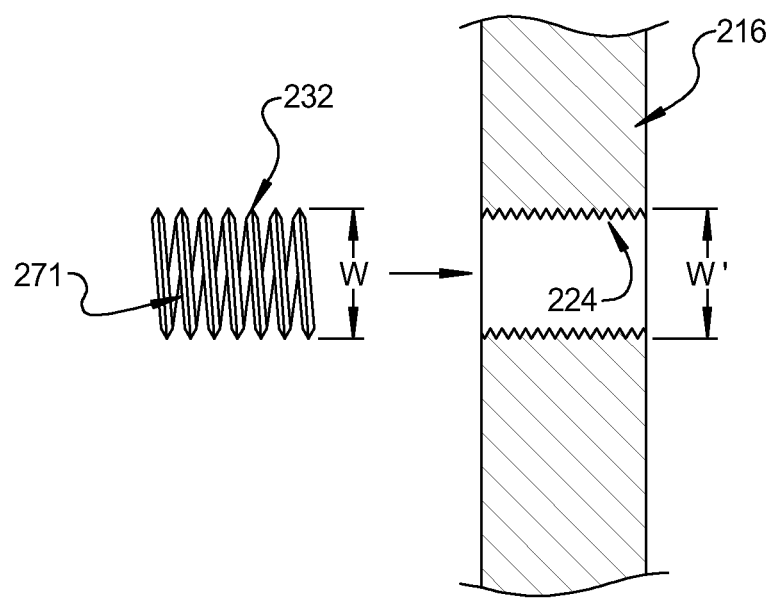
FIG. 7 is a partial sectional view of the system according to various additional exemplary embodiments, wherein a plug is shown before being coupled to an IM rod.
Figure 8:
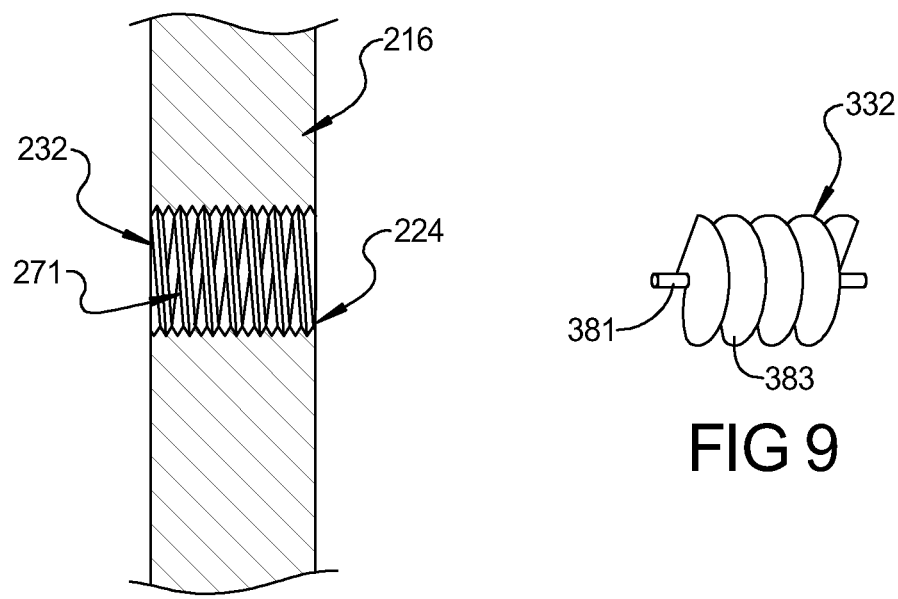
FIG. 8 is a partial sectional view of the system of FIG. 7, wherein the plug is shown coupled to the IM rod.

Referring now to FIGS. 7 and 8, additional exemplary embodiments of the present disclosure will be discussed. Components that are similar to the embodiments of FIGS. 1-4 are identified with corresponding reference numerals increased by 200. It will be appreciated that the components illustrated in FIGS. 7 and 8 can include similar features, can be made out of similar materials, and can provide similar advantages as those described above. Those details will not be repeated here; however, the embodiments of FIGS. 7 and 8 can include additional features as well, including those discussed below.

FIG. 7 shows another exemplary embodiment of the plug 232 before being inserted into the opening 224 of the rod 216. As shown, the plug 232 can be substantially helical and resiliently deformable. For instance, the plug 232 can helically wind about its axis to define an inner space 271 therein. Also, the plug 232 can have a width W that is greater than a width W' of the opening 224.

As such, when the plug 232 is inserted into the opening 224 (as indicated by an arrow in FIG. 7), the helical plug 232 can elastically and resiliently deform, reducing in width, to be retained securely within the opening 224.

Furthermore, to remove the plug 232, the removal tool 34 discussed above and shown in FIGS. 3 and 4 can at least partially enter the inner space 271 and engage the plug 232 (not specifically shown). As such, engaging the plug 232 for removal can be facilitated.

Figure 9:
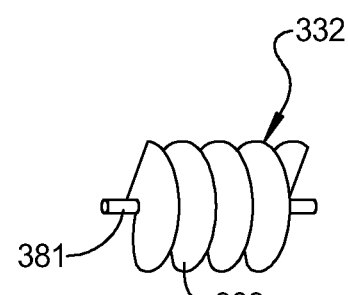
FIG. 9 is a perspective view of a plug of the system according to various additional embodiments of the present disclosure.

Referring now to FIG. 9, additional exemplary embodiments of the present disclosure will be discussed. Components that are similar to the embodiments of FIGS. 1-4 are identified with corresponding reference numerals increased by 300. It will be appreciated that the components illustrated in FIG. 9 can include similar features, can be made out of similar materials, and can provide similar advantages as those described above. Those details will not be repeated here; however, the embodiments of FIG. 9 can include additional features as well, including those discussed below.

As shown, the plug 332 can have an auger-type shape. For instance, the plug 332 can have a central rod 381 and a blade 383 that helically winds about the rod 381, similar to an auger. The shape of the plug 332 can facilitate coupling and de-coupling of the plug 332 because of the substantially small surface area contact with the rod 16, 116, 216.

Moreover, the foregoing discussion discloses and describes merely exemplary embodiments of the present disclosure. One skilled in the art will readily recognize from such discussion, and from the accompanying drawings and claims, that various changes, modifications and variations may be made therein without departing from the spirit and scope of the disclosure as defined in the following claims. For instance, the sequence of the blocks of the method described herein can be changed without departing from the scope of the present disclosure.

What is claimed is:

1. A system for implanting a prosthetic device into a bone, the prosthetic device having an opening that is disposed in the bone, the system comprising:
a plug that is removably received within the opening of the prosthetic device;
a bone removal tool that advances into the bone from outside the bone and that removes a portion of the bone while advancing into the bone to reveal the plug, the bone removal tool including a plug engaging portion that engages with the plug, the bone removal tool at least partially removing the plug from the opening of the prosthetic device while engaged with the plug; and
an alignment system that detects whether the bone removal tool and the plug are substantially axially aligned,
wherein the alignment system includes a receiver and a signal generator, one of the receiver and the signal generator being positioned within the plug.

2. The system of claim 1, wherein the plug is threadably engaged to the prosthetic device in the opening in a first rotational direction, and wherein the bone removal tool includes a drill bit that removes the portion of the bone by rotating in a second rotational direction, the second rotational direction being opposite the first rotational direction.

3. The system of claim 1, wherein the bone removal tool includes a drill bit that advances into the bone in a first direction to remove the portion of the bone, the drill bit engaging with the plug as the drill bit advances in the first direction, the plug being removable from the opening of the prosthetic device in a second direction, the second direction being opposite the first direction.

4. The system of claim 1, wherein the plug engaging portion includes a barb that embeds within the plug to engage with the plug.

5. The system of claim 1, wherein the alignment system includes an ultrasound system that is operatively coupled to the bone removal tool, and wherein the plug includes an ultrasonically detectable material that is detectable with an ultrasound signal generated by the ultrasound system, the ultrasound system distinguishing between the ultrasonically detectable material and an area adjacent the ultrasonically detectable material to detect whether the bone removal tool and the plug are substantially axially aligned.

6. The system of claim 1, wherein the alignment system includes a signal generator that generates and emits a radio frequency (RF) signal and a receiver that receives the RF signal, the signal generator being operably coupled to one of the plug and the bone removal tool, the receiver being operably coupled to the other of the plug and the bone removal tool, the alignment system also including a processor that detects whether the bone removal tool and the plug are substantially axially aligned based on the RF signal received by the receiver.

7. The system of claim 1, wherein the bone removal tool includes a drill bit, and further comprising a power generator that generates power from rotation of the drill bit to power the alignment system.

8. The system of claim 1, wherein the alignment system includes a feedback device that indicates that the bone removal tool is substantially axially aligned with the plug.

9. The system of claim 8, wherein the feedback system includes at least one of a visual feedback system, an audible feedback system, and a tactile feedback system.

10. The system of claim 1, further comprising the prosthetic device, and wherein the prosthetic device includes an intramedullary rod that is received within an intramedullary canal of the bone.

11. The system of claim 1, wherein the plug is axially tapered.

12. The system of claim 1, wherein the plug includes a deformable outer surface that deforms against an inner surface of the opening of the prosthetic device upon insertion of the plug into the opening of the prosthetic device.

13. The system of claim 12, wherein the deformable outer surface plastically deforms upon insertion of the plug into the opening.

14. A system for implanting a prosthetic device into a bone comprising:
an intramedullary (IM) rod that is operable to be implanted in an IM canal of one of a femur, a tibia, and a humerus, the IM rod having a longitudinal axis and a through hole that extends transverse to the longitudinal axis;
a plug that is threadably engaged to the IM rod within the through hole in a first rotational direction;
a bone removal tool that rotates in a second rotational direction, the second rotational direction being opposite the first rotational direction, the bone removal tool advancing into the bone from outside the bone in a first linear direction, the bone removal tool removing a portion of the bone while rotating in the second rotational direction and while advancing through the bone in the first linear direction to reveal the plug, the bone removal tool including a barb that embeds within and engages with the plug, the bone removal tool at least partially threadably disengaging the plug from the through hole of the IM rod while rotating in the second rotational direction and while embedded within the plug;
an alignment system that detects whether the bone removal tool and the plug are substantially axially aligned, the alignment system including at least one of an ultrasound system and a proximity sensor system, the alignment system including a power generating device that generates power from rotation of the bone removal tool to power the alignment system;
a feedback device that indicates that the bone removal tool is substantially axially aligned with the plug; and
a fastener that extends into the bone and into the opening to secure the intramedullary rod to the bone.

15. The system of claim 14, wherein the proximity sensor system is a radio frequency system.

16. The system of claim 15, wherein the plug further includes a passive signal generator and the bone removing tool includes a transceiver that emits a field to cause the passive signal generator to emit a radio frequency signal.

17. The system of claim 14, wherein the feedback device provides a feedback signal selected from the group comprising visual feedback, an audible feedback, a tactile feedback, and combinations thereof.

18. A system for implanting a prosthetic device into a bone, the prosthetic device having an opening that is disposed in the bone, the system comprising:
a plug configured to be removably received within the opening of the prosthetic device, the plug including a signal generator positioned within the plug and configured to emit a radio frequency signal;
a bone removal tool configured to pass into the bone relative to the plug, the bone removal tool including a plug engaging portion configured to engage the plug to at least partially remove the plug from the opening of the prosthetic device while engaging the plug; and an alignment system that detects whether the bone removal tool and the plug are substantially axially aligned, the alignment system including a receiver that receives the radio frequency signal from the signal generator associated with the plug and a processor that detects whether the bone removal tool and the plug are substantially axially aligned based on the radio frequency signal received by the receiver.

19. The system of claim 18, wherein the plug is threadably engaged to the prosthetic device in the opening in a first rotational direction, and wherein the bone removal tool includes a drill bit that removes a portion of the bone by rotating in a second rotational direction, the second rotational direction being opposite the first rotational direction.

20. The system of claim 18, wherein the bone removal tool includes a drill bit that advances into the bone in a first direction to remove a portion of the bone, the drill bit engaging with the plug as the drill bit advances in the first direction, the plug being removable from the opening of the prosthetic device in a second direction, the second direction being opposite the first direction.

21. The system of claim 18, wherein the alignment system includes a feedback device that indicates that the bone removal tool is substantially axially aligned with the plug.

22. The system of claim 18, further comprising the prosthetic device, and wherein the prosthetic device includes an intramedullary rod that is received within an intramedullary canal of the bone.

23. The system of claim 18, wherein the plug engaging portion includes a barb that embeds within the plug to engage with the plug.

24. The system of claim 18, wherein the signal generator is a passive signal generator and the receiver is a transceiver that emits a field that causes the signal generator to emit the radio frequency signal.

25. The system of claim 18, wherein the alignment system further includes a feedback device having an indicator that provides a feedback signal if the bone removal tool is substantially axially aligned with the plug selected from the group consisting of a visual feedback, an audible feedback, a tactile feedback, and combinations thereof.

* * * * *